(12) United States Patent
Gerlach et al.

(10) Patent No.: US 7,034,186 B2
(45) Date of Patent: Apr. 25, 2006

(54) PREPARATION OF AN AMINE

(75) Inventors: Till Gerlach, Ludwigshafen (DE); Frank Funke, Ludwigshafen (DE); Johann-Peter Melder, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 48 days.

(21) Appl. No.: 10/731,158

(22) Filed: Dec. 10, 2003

(65) Prior Publication Data

US 2004/0122259 A1  Jun. 24, 2004

(30) Foreign Application Priority Data

Dec. 20, 2002  (DE) ................. 102 61 193

(51) Int. Cl.
  *C07C 209/26*  (2006.01)
  *C07C 209/16*  (2006.01)
  *C07C 209/18*  (2006.01)

(52) U.S. Cl. .............. 564/473; 564/397; 564/398; 564/401; 564/402; 564/403; 564/472; 564/479; 564/480

(58) Field of Classification Search ............. 564/397, 564/398, 401–403, 472, 473, 479, 480
See application file for complete search history.

(56) References Cited

U.S. PATENT DOCUMENTS

| 4,152,353 A | 5/1979 | Habermann |
| 5,002,922 A | 3/1991 | Irgang et al. |
| 5,530,127 A | 6/1996 | Reif et al. |
| 6,057,442 A | 5/2000 | Wulff-Doring |
| 6,111,141 A | 8/2000 | Eller et al. |
| 6,417,353 B1 | 7/2002 | Funke et al. |
| 6,525,222 B1 | 2/2003 | Nouwen et al. |
| 6,563,004 B1 | 5/2003 | Nouwen et al. |

FOREIGN PATENT DOCUMENTS

| DE | 26 18 580 | 11/1977 |
| EP | 17 651 | 10/1980 |
| EP | 382 049 | 8/1990 |
| EP | 514 692 | 11/1992 |
| EP | 696 572 | 2/1996 |
| EP | 905 122 | 3/1999 |
| EP | 963 975 | 12/1999 |
| EP | 1 020424 | 7/2000 |
| EP | 1 035106 | 9/2000 |
| EP | 1 106600 | 6/2001 |
| EP | 1 106601 | 6/2001 |

OTHER PUBLICATIONS

Derwent Abst. 77 75909, 1977.
Derwent Abst. 92-391015, 1992.
Abst 2000-099348/09, 2000.

*Primary Examiner*—Brian Davis
(74) *Attorney, Agent, or Firm*—Novak Druce Deluca & Quigg, LLP

(57) ABSTRACT

Process for preparing an amine by reacting a primary or secondary alcohol, aldehyde or ketone with hydrogen and a nitrogen compound selected from the group consisting of ammonia and primary and secondary amines in the presence of a catalyst whose preparation has involved precipitation of catalytically active components onto monoclinic, tetragonal or cubic zirconium dioxide.

12 Claims, 1 Drawing Sheet

PREPARATION OF AN AMINE

Figure 1:
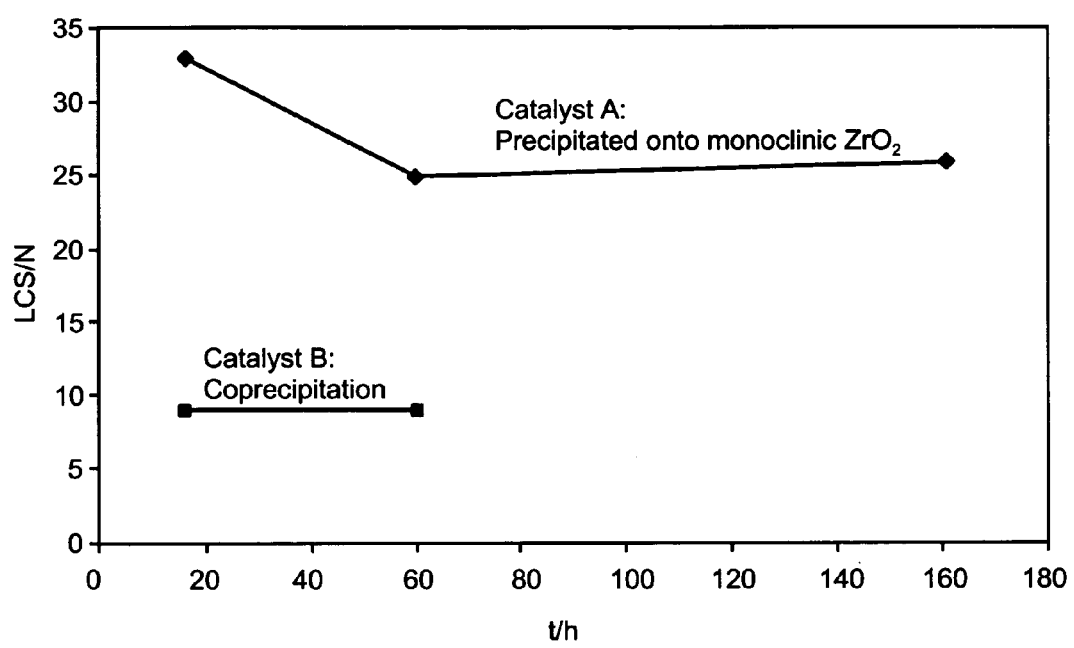

The present invention relates to a process for preparing an amine by reacting a primary or secondary alcohol, aldehyde or ketone with hydrogen and a nitrogen compound selected from the group consisting of ammonia and primary and secondary amines in the presence of a catalyst.

DE-A1-26 18 580 (BASF AG) describes a process for preparing tertiary amines in the presence of an essentially support-free catalyst comprising at least 60% of Co and from about 10 to 30% of Cu, with up to 20% of the cobalt being able to be replaced by Ni.

EP-A2-514 692 (BASF AG) discloses a process for preparing amines from alcohols in the presence of catalysts comprising copper and nickel and zirconium oxide and/or aluminum oxide.

EP-A1-382 049 (BASF AG) relates to catalysts comprising zirconium oxide, copper, cobalt and nickel and their use in processes for preparing amines from alcohols or carbonyl compounds.

EP-A1-696 572, EP-A2-905 122, EP-A1-963 975, EP-A1-1 035 106, EP-A2-1 106 600 and the earlier German patent application No. 10211101.4 of Mar. 14, 2002 (all BASF AG) describe catalysts comprising zirconium oxide, copper oxide and nickel oxide and their use in processes for preparing amines from alcohols or aldehydes or ketones.

EP-A1-17 651 and U.S. Pat. No. 4,152,353 (both Dow Chem. Company) relate to catalysts for the amination of alcohols, aldehydes or ketones, which catalysts comprise Ni or Co, Cu and (Fe, Zn or Zr) (claim 1).

The catalysts of the prior art which comprise zirconium oxide are preferably obtainable by coprecipitation of water-soluble compounds of appropriate metals including zirconium by means of mineral bases and subsequent drying and heat treatment (cf., for example, EP-A1-696 572, page 6, lines 7 to 16, and EP-A1-382 049, page 3, lines 25 to 35).

However, it is also possible firstly to precipitate the zirconium components separately and then precipitate the remaining metal compounds (e.g. copper and nickel compounds) in the presence of the previously precipitated hydrated zirconium oxide (cf., for example, EP-A1-696 572, page 6, lines 17 to 23, and EP-A1-382 049, page 3, lines 14 to 24 and 36 to 43).

EP-A1-1 020 424 and EP-A1-1 106 601 (both BASF AG) describe the preparation of supported catalysts for the amination of acetaldehyde or acetone by impregnation of the support material with appropriate metal salt solutions. Among the numerous support materials suitable for the impregnation, mention is made of zirconium dioxide in the monoclinic or tetragonal form.

A parallel German patent application (BASF AG) filed on the same day relates to a process for the catalytic hydrogenation of an aliphatically unsaturated group in an organic compound using a catalyst whose preparation has involved precipitation of catalytically active components onto monoclinic, tetragonal or cubic zirconium dioxide.

A parallel German patent application (BASF AG) filed on the same day relates to a process for preparing a symmetrical secondary amine by reaction of a primary amine in the presence of hydrogen and a catalyst whose preparation has involved precipitation of catalytically active components onto monoclinic, tetragonal or cubic zirconium dioxide.

A disadvantage of the heterogeneous catalysts of the prior art which comprise zirconium dioxide in the amination of alcohols, aldehydes and ketones is, as has been recognized according to the present invention, the decrease in their mechanical stability under the reaction conditions under which they are used, in particular in the presence of reaction media comprising water. In such a case, the water can be initially present in the reaction feed or be formed as product during the amination reaction. A consequence of less mechanically stable heterogeneous catalysts is the necessity of changing the catalyst in the reactor more frequently and thus a reduced space-time yield.

It is an object of the present invention to remedy the disadvantages of the prior art and to provide an improved process for preparing amines from alcohols, aldehydes and ketones using a catalyst having improved mechanical properties under the reaction conditions of its use and thus to improve the economics of previous processes, in particular those in which catalysts comprising zirconium dioxide are used.

According to the present invention, it has been recognized that a reason for the not fully satisfactory mechanical stability, i.e. the mechanical softening, of the known catalysts comprising zirconium dioxide under reaction conditions is the fact that, for example when the abovementioned (co)precipitation technique is employed, zirconium dioxide is initially present in wholly or partially amorphous form and under the conditions of the chemical reaction catalyzed by means of these catalysts undergoes a complete or partial crystallization, i.e. conversion of the modification into tetragonal, monoclinic or cubic zirconium dioxide. In amination reactions, the reaction conditions employed usually involve elevated temperature (e.g. 80–300° C.) and elevated pressure (e.g. 50–300 bar in the case of liquid-phase aminations or 1–400 bar in the case of gas-phase aminations). In addition, the reaction media comprise water.

We have found that the use of zirconium dioxide which is in a modification which is thermodynamically stable or at least metastable under the reaction conditions of the amination reaction, e.g. monoclinic, tetragonal or cubic zirconium dioxide, in the preparation of a catalyst comprising zirconium dioxide significantly increases the mechanical stability of the resulting catalysts under the reaction conditions, particularly in the presence of reaction media comprising water.

The present invention accordingly provides a process for preparing an amine by reacting a primary or secondary alcohol, aldehyde or ketone with hydrogen and a nitrogen compound selected from the group consisting of ammonia and primary and secondary amines in the presence of a catalyst whose preparation has involved precipitation of catalytically active components onto monoclinic, tetragonal or cubic zirconium dioxide.

The catalytically active components precipitated on are, in particular, salts of metals selected from groups 8 to 11 (corresponding to transition groups VIII and IB) of the Periodic Table of the Elements, especially from the group consisting of Fe, Co, Ni, Ru, Rh, Pd, Pt and Cu. The metal is particularly preferably selected from the group consisting of Cu, Ni and Co.

In general, the catalysts in the process of the present invention are preferably used in the form of catalysts which consist entirely of catalytically active composition and possibly a shaping aid (e.g. graphite or stearic acid) if the catalyst is used as shaped bodies, i.e. contain no further catalytically inactive constituents.

The catalytically active composition can be introduced into the reaction vessel after milling as power or as cross material or, preferably, introduced into the reactor after milling, mixing with shaping aids, shaping and heat treatment as shaped catalyst bodies, for example as pellets, spheres, rings, extrudates (e.g. rods).

The abovementioned concentrations (in % by weight) of the components of the catalyst are based, unless indicated otherwise, on the catalytically active composition of the catalyst prepared before treatment with hydrogen.

The catalytically active composition of the catalyst is defined as the sum of the catalytically active constituents and the composition comprises, before treatment with hydrogen, essentially the catalytically active constituents monoclinic, tetragonal or cubic zirconium dioxide (or mixtures of these modifications) and metal salts as further catalytically active components.

The sum of the abovementioned catalytically active constituents, calculated in oxidic form, e.g. as $ZrO_2$, CuO, NiO and CoO, in the catalytically active composition before treatment with hydrogen is generally from 70 to 100% by weight, preferably from 80 to 100% by weight, particularly preferably from 90 to 100% by weight, in particular from 95 to 100% by weight, very particularly preferably from >98 to 100% by weight.

The catalytically active composition of the catalysts used in the process of the present invention can further comprise one or more elements (oxidation state 0), or inorganic or organic compounds thereof, selected from groups IA to VIA and IB to VIIB and VIII of the Periodic Table.

Examples of such elements and compounds thereof are:

Transition metals such as Mn and manganese oxides, Re and rhenium oxides, Cr and chromium oxides, Mo and molybdenum oxides, W and tungsten oxides, Ta and tantalum oxides, Nb and niobium oxides or niobium oxalate, V and vanadium oxides or vanadyl pyrophosphate, zinc and zinc oxides, silver and silver oxides, lanthanides such as Ce and $CeO_2$ or Pr and $Pr_2O_3$, alkali metal oxides such as $Na_2O$, alkali metal carbonates such as $Na_2CO_3$ and $K_2CO_3$, alkaline earth metal oxides such as SrO, alkaline earth metal carbonates such as $MgCO_3$, $CaCO_3$, $BaCO_3$, phosphoric anhydrides and boron oxide ($B_2O_3$).

The catalytically active composition of preferred catalysts for use in the process of the present invention comprises, before treatment with hydrogen, from 20 to 85% by weight, preferably from 20 to 65% by weight, particularly preferably from 22 to 40% by weight, of monoclinic, tetragonal or cubic zirconium dioxide ($ZrO_2$) (or mixtures of these modifications), from 1 to 30% by weight, particularly preferably from 2 to 25% by weight, of oxygen-containing compounds of copper, calculated as CuO, and from 14 to 70% by weight, preferably from 15 to 50% by weight, particularly preferably from 21 to 45% by weight, of oxygen-containing compounds of nickel, calculated as NiO, with the molar ratio of nickel to copper preferably being greater than 1, in particular greater than 1.2, very particularly preferably from 1.8 to 8.5.

The catalytically active composition of particularly preferred catalysts further comprises, before treatment with hydrogen, from 15 to 50% by weight, particularly preferably from 21 to 45% by weight, of oxygen-containing compounds of cobalt, calculated as CoO.

The oxygen-containing compounds of copper, nickel and, if applicable, cobalt, each calculated as CuO, NiO and CoO, of the preferred catalysts are generally present in the catalytically active composition (before treatment with hydrogen) in total amounts of from 15 to 80% by weight, preferably from 35 to 80% by weight, particularly preferably from 60 to 78% by weight, with the molar ratio of nickel to copper particularly preferably being greater than 1.

The catalysts used according to the present invention can be prepared as follows.

In the preparation of the catalysts, the term "precipitation onto" refers to a procedure in which a sparingly soluble support material is suspended in a liquid, usually water, the doping components are used as readily soluble compounds and are dissolved in a liquid, usually water, and are then precipitated onto the suspended support by addition of a precipitant (e.g. as described in EP-A2-1 106 600, page 4, and A. B. Stiles, Catalyst Manufacture, Marcel Dekker, Inc., 1983, page 15).

According to the present invention, the support material used for preparation of the catalyst is zirconium dioxide in a thermodynamically stable or metastable modification, i.e. in the monoclinic, tetragonal or cubic modification.

The basic properties of zirconium dioxide are summarized in

K. Dyrek, A. Adamski, Z. Sojka, Ceramic Interfaces 2, University Press, Cambridge, 2001, pp. 241–259, including the monoclinic, tetragonal and cubic modifications which exist and their preparation.

The zirconium dioxide crystal structure can, particularly in the case of the tetragonal modification, be stabilized further by additions of one or more oxides of metals of transition group IIIB or main group IIA of the Periodic Table, in particular yttrium oxide, calcium oxide, lanthanum oxide, magnesium oxide or scandium oxide.

This stabilization effects, for example, total or partial inhibition of the conversion of the tetragonal modification into the most thermodynamically stable monoclinic modification.

To prepare the catalyst, the zirconium dioxide is suspended in a solvent, e.g. in water. The metal salts dissolved, for example, in water are then added and basic salts which are sparingly soluble or insoluble in the solvent used, e.g. water, are subsequently precipitated by addition of, for example, an alkali metal hydroxide.

The precipitates obtained in these precipitation reactions are generally not chemically uniform and usually comprise mixtures of oxides, hydrated oxides, hydroxides, carbonates and/or hydrogencarbonates of the metals used.

The precipitation can, for example, be carried out at 20–100° C., in particular 50–90° C., especially 60–80° C.

As an alternative, the metal salt solution and the alkali can be introduced simultaneously into a vessel in which the zirconium dioxide support suspension is present. The support can also be suspended in the metal salt solution and this can be introduced into a precipitation vessel simultaneously with the alkali.

The further catalyst preparation is then carried out by known methods, e.g. filtration, washing, drying, calcination, shaping, reduction/passivation.

The catalysts prepared in this way comprise, prior to reduction/passivation, the catalytically active metals in the form of a mixture of their oxygen-containing compounds, in particular as oxides and mixed oxides.

The catalysts can be stored as such after their preparation. Before use as catalysts for the hydrogenative amination of alcohols, aldehydes or ketones, they are usually prereduced by treatment with hydrogen. However, they can also be used without prereduction, in which case they are then reduced under the conditions of the hydrogenative amination by the hydrogen present in the reactor. To carry out the prereduction, the catalysts are generally firstly exposed to a nitrogen/hydrogen atmosphere at from 150 to 200° C. for a period of from 12 to 20 hours and subsequently treated in a hydrogen atmosphere at from 200 to 400° C. for up to about 24 hours. In this prereduction, part of the oxygen-containing metal compounds present in the catalysts is reduced to the corresponding metals, so that these are present together with the various oxygen compounds in the active form of the catalyst.

Amines of the formula I

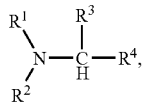

(I)

where $R^1$, $R^2$ are each hydrogen (H), alkyl such as $C_{1-20}$-alkyl, cycloalkyl such as $C_{3-12}$-cycloalkyl, alkoxyalkyl such as $C_{2-30}$-alkoxyalkyl, dialkylaminoalkyl such as $C_{3-30}$-dialkylaminoalkyl, aryl, aralkyl such as $C_{7-20}$-aralkyl or alkylaryl such as $C_{7-20}$-alkylaryl, or together form —$(CH_2)_j$—X—$(CH_2)_k$—, $R^3$, $R^4$ are each hydrogen (H), alkyl such as $C_{1-200}$-alkyl, cycloalkyl such as $C_{3-12}$-cycloalkyl, hydroxyalkyl such as $C_{1-20}$-hydroxyalkyl, aminoalkyl such as $C_{1-20}$-aminoalkyl, hydroxyalkylaminoalkyl such as $C_{2-20}$-hydroxyalkylaminoalkyl, alkoxyalkyl such as $C_{2-30}$-alkoxyalkyl, dialkylaminoalkyl such as $C_{3-30}$-dialkylaminoalkyl, alkylaminoalkyl such as $C_{2-30}$-alkylaminoalkyl, $R^5$—(OCR$^6$R$^7$CR$^8$R$^9$)$_n$—(OCR$^6$R$^7$), aryl, heteroaryl, aralkyl such as $C_{7-20}$-aralkyl, heteroarylalkyl such as $C_{4-20}$-heteroarylalkyl, alkylaryl such as $C_{7-20}$-alkylaryl, alkylheteroaryl such as $C_{4-20}$-alkylheteroaryl or Y—$(CH_2)_m$—NR$^5$—$(CH_2)_q$, or together form —$(CH_2)_l$—X—$(CH_2)_m$—, or $R^2$ and $R^4$ together form —$(CH_2)_l$—X—$(CH_2)_m$—, $R^5$, $R^{10}$ are each hydrogen (H), alkyl such as $C_{1-4}$-alkyl or alkylphenyl such as $C_{7-40}$-alkylphenyl, $R^6$, $R^7$, $R^8$, $R^9$ are each hydrogen (H), methyl or ethyl, X is $CH_2$, CHR$^5$, oxygen (O), sulfur (S) or NR$^5$, Y is N(R$^{10}$)$_2$, hydroxy, $C_{2-20}$-alkylaminoalkyl or $C_{3-20}$-dialkylaminoalkyl, n is an integer from 1 to 30 and j, k, l, m, q are each an integer from 1 to 4, are of particular economic interest.

The process of the present invention is therefore preferably employed for preparing an amine I by reacting a primary or secondary alcohol of the formula II

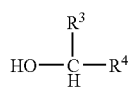

(II)

or an aldehyde or ketone of the formula VI or VII

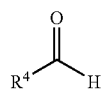

(VI)

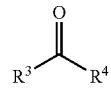

(VII)

with a nitrogen compound of the formula III

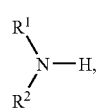

(III)

where $R^1$, $R^2$, $R^3$ and $R^4$ are as defined above.

As indicated by the definitions of the radicals $R^2$ and $R^4$, the reaction can also be carried out intramolecularly in an appropriate amino alcohol, amino ketone or amino aldehyde.

Accordingly, in purely formal terms, the amine I is prepared by replacement of a hydrogen atom of the nitrogen compound III by the radical $R^4(R^3)$CH— with liberation of one molar equivalent of water.

Preference is also given to employing the process of the present invention in the preparation of a cyclic amine of the formula IV

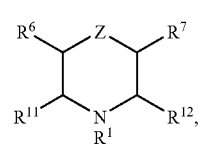

(IV)

where $R^{11}$ and $R^{12}$ are each hydrogen (H), alkyl such as $C_1$–$C_{20}$-alkyl, cycloalkyl such as $C_3$–$C_{12}$-cycloalkyl, aryl, heteroaryl, aralkyl such as $C_7$–$C_{20}$-aralkyl and alkylaryl such as $C_7$–$C_{20}$-alkylaryl, Z is $CH_2$, CHR$^5$, oxygen (O), NR$^5$ or NCH$_2$CH$_2$OH and $R^1$, $R^6$, $R^7$ are as defined above, by reaction of an alcohol of the formula V

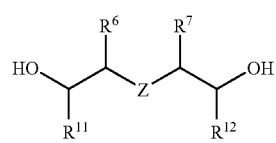

(V)

with ammonia or a primary amine of the formula VI

—NH$_2$ (VI).

The substituents $R^1$ to $R^{12}$, the variables X, Y, Z and the indices j, k, l, m, n and q in the compounds I, II, III, IV, V, VI and VII independently have the following meanings:

$R^1$, $R^2$, $R^3$, $R^4$, $R^5$, $R^6$, $R^7$, $R^8$, $R^9$, $R^{10}$, $R^{11}$, $R^{12}$: hydrogen (H), $R^3$, $R^4$:
alkyl such as $C_{1-200}$-alkyl, preferably $C_{1-14}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, particularly preferably isopropyl, 2-ethylhexyl, n-decyl, 2-n-propyl-n-heptyl, n-tridecyl, 2-n-butyl-n-nonyl and 3-n-butyl-n-nonyl, and also preferably $C_{40-200}$-alkyl such as polybutyl, polyisobutyl, polypropyl, polyisopropyl and polyethyl, particularly preferably polybutyl and polyisobutyl, hydroxyalkyl such as $C_{1-20}$-hydroxyalkyl, preferably $C_{1-8}$-hydroxyalkyl, particularly preferably $C_{1-4}$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-(hydroxymethyl) ethyl, aminoalkyl such as $C_{1-20}$-aminoalkyl, preferably $C_{1-8}$-aminoalkyl such as aminomethyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl) aminomethyl, hydroxyalkylaminoalkyl such as $C_{2-20}$-hydroxyalkylaminoalkyl, preferably $C_{3-8}$-hydroxyalkylaminoalkyl such as (2-hydroxyethylamino)methyl, 2-(2-hydroxyethylamino)ethyl and 3-(2-hydroxyethylamino)propyl, $R^5$—$(OCR^6R^7CR^8R^9)_n$—$(OCR^6R^7)$, preferably $R^5$—$(OCHR^7CHR^9)_n$—$((OCR^6R^7)$, particularly preferably $R^5$—$(OCH_2CHR^9)_n$—$(OCR^6R^7)$, alkylaminoalkyl such as $C_{2-30}$-alkylaminoalkyl, preferably $C_{2-20}$-alkylaminoalkyl, particularly preferably $C_{2-8}$-alkylaminoalkyl such as methylaminomethyl, 2-methylaminoethyl, ethylaminomethyl, 2-ethylaminoethyl and 2-(isopropylamino)ethyl, $(R^5)HN$—$(CH_2)_q$, $Y$—$(CH_2)_m$—$NR^5$—$(CH_2)_q$, heteroarylalkyl such as $C_{4-20}$-heteroarylalkyl, e.g. pyrid-2-yl-methyl, furan-2-yl-methyl, pyrrol-3-yl-methyl and imidazol-2-yl-methyl, alkylheteroaryl such as $C_{4-20}$-alkylheteroaryl, e.g. 2-methyl-3-pyridinyl, 4,5-dimethyl-imidazol-2-yl, 3-methyl-2-furanyl and 5-methyl-2-pyrazinyl, heteroaryl such as 2-pyridinyl, 3-pyridinyl, 4-pyridinyl, pyrazinyl, pyrrol-3-yl, imidazol-2-yl, 2-furanyl and 3-furanyl, $R^1$, $R^2$, $R^3$, $R^4$:

cycloalkyl such as $C_{3-12}$-cycloalkyl, preferably $C_{3-8}$-cycloalkyl such as cyclopropyl, cyclobutyl, cyclopentyl, cyclohexyl, cycloheptyl and cyclooctyl, particularly preferably cyclopentyl and cyclohexyl, alkoxyalkyl such as $C_{2-30}$-alkoxyalkyl, preferably $C_{2-20}$-alkoxyalkyl, particularly preferably $C_{2-8}$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_{2-4}$-alkoxyalkyl, dialkylaminoalkyl such as $C_{3-30}$-dialkylaminoalkyl, preferably $C_{3-20}$-dialkylaminoalkyl, particularly preferably $C_{3-10}$-dialkylaminoalkyl such as N,N-dimethylaminomethyl, (N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino)ethyl and 2-(N,N-diisopropylamino)ethyl, 3-(N,N-dimethylamino)propyl, $(R^5)_2N$—$(CH_2)_q$, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, alkylaryl such as $C_{7-20}$-alkylaryl, preferably $C_{7-12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, aralkyl such as $C_{7-20}$-aralkyl, preferably $C_{7-12}$-phenylalkyl such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $R^3$ and $R^4$ or $R^2$ and $R^4$ together form a —$(CH_2)_l$—$X$—$(CH_2)_m$— group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)$—$CHR^5$—$(CH_2)_2$—, —$(CH_2)_2$—O—$(CH_2)_2$—, —$(CH_2)_2$—$NR^5$—$(CH_2)_2$—, —$(CH_2)_2$—$CHR^5$—$(CH_2)_2$—, —$CH_2$—O—$(CH_2)_3$—, —$CH_2$—$NR^5$—$(CH_2)_3$—, —$CH_2$—$CHR^5$—$(CH_2)_3$—, $R^1$, $R^2$:

alkyl such as $C_{1-20}$-alkyl, preferably $C_{1-8}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, particularly preferably $C_{1-4}$-alkyl, or $R^1$ and $R^2$ together form a —$(CH_2)_j X$—$(CH_2)_k$— group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^5$—$(CH_2)_2$—, —$(CH_2)$—$CHR^5$—$(CH_2)_2$—, —$(CH_2)_2$—O—$(CH_2)_2$—, —$(CH_2)_2$—$NR^5$—$(CH_2)_2$—, —$(CH_2)_2$—$CHR^5$—$(CH_2)_2$—, —$CH_2$—O—$(CH_2)_3$—, —$CH_2$—$NR^5$—$(CH_2)_3$—, —$CH_2$—$CHR^5$—$(CH_2)_3$—, $R^5$, $R^{10}$:

alkyl, preferably $C_{1-4}$-alkyl such as methyl, ethyl, n-propyl, isopropyl, n-butyl, isobutyl, sec-butyl and tert-butyl, preferably methyl and ethyl, particularly preferably methyl, alkylphenyl, preferably $C_{7-40}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, $R^6$, $R^7$, $R^8$, $R^9$:

methyl or ethyl, preferably methyl, $R^{11}$, $R^{12}$:

alkyl such as $C_1$–$C_{20}$-alkyl, cycloalkyl such as $C_3$–$C_{12}$-cycloalkyl, aryl, heteroaryl, aralkyl such as $C_7$–$C_{20}$-aralkyl and alkylaryl such as $C_7$–$C_{20}$-alkylaryl, each as defined above,

X:

$CH_2$, $CHR^5$, oxygen (O), sulfur (S) or $NR^5$, preferably $CH_2$ and O,

Y:

$N(R^{10})_2$, preferably $NH_2$ and $N(CH_3)_2$, hydroxy (OH),

C$_{2-20}$-alkylaminoalkyl, preferably C$_{2-16}$-alkylaminoalkyl such as methylaminomethyl, 2-methylaminoethyl, ethylaminomethyl, 2-ethylaminoethyl and 2-(isopropylamino)ethyl, C$_{3-20}$-dialkylaminoalkyl, preferably C$_{3-16}$-dialkylaminoalkyl such as dimethylaminomethyl, 2-dimethylaminoethyl, 2-diethylaminoethyl, 2-(di-n-propylamino) ethyl and 2-(diisopropylamino)ethyl, Z:
CH$_2$, CHR$^5$, O, NR$^5$ or NCH$_2$CH$_2$OH, j, l:
an integer from 1 to 4 (1, 2, 3 or 4), preferably 2 and 3, particularly preferably 2, k, m, q:
an integer from 1 to 4 (1, 2, 3 or 4), preferably 2, 3 and 4, particularly preferably 2 and 3, n:
an integer from 1 to 30, preferably an integer from 1 to 8 (1, 2, 3, 4, 5, 6, 7 or 8), particularly preferably an integer from 1 to 6.

Suitable alcohols are virtually all primary and secondary alcohols having an aliphatic OH function. The alcohols can be linear, branched or cyclic. Secondary alcohols are aminated the same as primary alcohols. There are virtually no restrictions on the number of carbon atoms in the aminatable alcohols. The alcohols may also bear further substituents or contain functional groups which are inert under the conditions of the hydrogenative amination, for example, alkoxy, alkenyloxy, alkylamino or dialkylamino groups, or are hydrogenated under the conditions of the hydrogenative amination, for example CC double or triple bonds. If polyhydric alcohols are to be aminated, control of the reaction conditions allows amino alcohols, cyclic amines or multiply aminated products to be obtained preferentially.

The amination of 1,4-diols leads, depending on the reaction conditions chosen, to 1-amino-4-hydroxy compounds, 1,4-diamino compounds or five-membered rings containing a nitrogen atom (pyrrolidines).

The amination of 1,6-diols leads, depending on the reaction conditions chosen, to 1-amino-6-hydroxy compounds, 1,6-diamino compounds or seven-membered rings containing a nitrogen atom (hexamethylenimines).

The amination of 1,5-diols leads, depending on the reaction conditions chosen, to 1-amino-5-hydroxy compounds, 1,5-diamino compounds or six-membered rings containing a nitrogen atom (piperidines). Accordingly, diglycol can be aminated by NH$_3$ to give monoaminodiglycol (=ADG=H$_2$N—CH$_2$CH$_2$—O—CH$_2$CH$_2$—OH), diaminodiglycol or particularly preferably morpholine.

Correspondingly, diethanolamine is particularly preferably converted into piperazine. N-(2-Hydroxyethyl)piperazine can be obtained from triethanolamine.

Preference is given, for example, to aminating the following alcohols:

methanol, ethanol, n-propanol, isopropanol, n-butanol, isobutanol, tert-butanol, n-pentanol, n-hexanol, 2-ethylhexanol, tridecanol, stearyl alcohol, palmityl alcohol, cyclobutanol, cyclopentanol, cyclohexanol, benzyl alcohol, 2-phenylethanol, 2-(p-methoxyphenyl)ethanol, 2-(3,4-dimethoxyphenyl)ethanol, 1-phenyl-3-butanol, ethanolamine, n-propanolamine, isopropanolamine, 2-amino-1-propanol, 1-methoxy-2-propanol, 3-amino-2,2-dimethyl-1-propanol, n-pentanolamine (1-amino-5-pentanol), n-hexanolamine (1-amino-6-hexanol), ethanolamine, diethanolamine, triethanolamine, N-alkyldiethanolamine, diisopropanolamine, 3-(2-hydroxyethylamino)propan-1-ol, 2-(N,N-dimethylamino)ethanol, 2-(N,N-diethylamino)ethanol, 2-(N,N-di-n-propylamino)ethanol, 2-(N,N-diisopropylamino)ethanol, 2-(N,N-di-n-butylamino)ethanol, 2-(N,N-diisobutylamino)ethanol, 2-(N,N-di-sec-butylamino)ethanol, 2-(N,N-di-tert-butylamino)ethanol, 3-(N,N-dimethylamino)propanol, 3-(N,N-diethylamino)propanol, 3-(N,N-di-n-propylamino)propanol, 3-(N,N-diisopropylamino)propanol, 3-(N,N-di-n-butylamino)propanol, 3-(N,N-diisobutylamino)propanol, 3-(N,N-di-sec-butylamino)propanol, 3-(N,N-di-tert-butylamino)propanol, 1-dimethylamino-4-pentanol, 1-diethylamino-4-pentanol, ethylene glycol, 1,2-propylene glycol, 1,3-propylene glycol, diglycol, 1,4-butanediol, 1,5-pentanediol, 1,6-hexanediol, 2,2-bis[4-hydroxycyclohexyl]propane, methoxyethanol, propoxyethanol, butoxyethanol, polyisobutyl alcohols, polypropyl alcohols, polyethylene glycol ethers, polypropylene glycol ethers and polybutylene glycol ethers. In the reaction according to the present invention, the polyalkylene glycol ethers mentioned are converted into the corresponding amines by transformation of their free hydroxyl groups.

Particularly preferred alcohols are methanol, ethanol, n-propanol, i-propanol, n-butanol, sec-butanol, 2-ethylhexanol, fatty alcohols, ethylene glycol, diethylene glycol, 2-(2-dimethylaminoethoxy)ethanol, N-methyldiethanolamine and 2-(2-dimethylaminoethoxy)ethanol.

Virtually all aliphatic and aromatic ketones are suitable for use in the process of the present invention. The aliphatic ketones can be linear, branched or cyclic, and the ketones can contain heteroatoms. There are virtually no restrictions on the number of carbon atoms in the aminatable ketones. The ketones can bear further substituents or contain functional groups which are inert under the conditions of the hydrogenative amination, for example alkoxy, alkenyloxy, alkylamino or dialkylamino groups, or are hydrogenated under the conditions of the hydrogenative amination, for example CC double or triple bonds. If polyfunctional ketones are to be aminated, control of the reaction conditions allows amino ketones, amino alcohols, cyclic amines or multiply aminated products to be obtained.

Preference is given, for example, to aminatively hydrogenating the following ketones:

acetone, ethyl methyl ketone, methyl vinyl ketone, isobutyl methyl ketone, 3-methylbutan-2-one, diethyl ketone, tetralon, acetophenone, p-methylacetophenone, p-methoxyacetophenone, m-methoxyacetophenone, 1-acetylnaphthalene, 2-acetyinaphthalene, 1-phenyl-3-butanone, cyclobutanone, cyclopentanone, cyclopentenone, cyclohexanone, cyclohexenone, 2,6-dimethylcyclohexanone, cycloheptanone, cyclododecanone, acetylacetone, methyl glyoxal and benzophenone.

Virtually all aliphatic and aromatic aldehydes are suitable for use in the process of the present invention. The aliphatic aldehydes can be linear, branched or cyclic, and can contain heteroatoms. There are virtually no restrictions on the number of carbon atoms in the aminatable aldehydes. The aldehydes can bear further substituents or contain functional groups which are inert under the conditions of the hydrogenative amination, for example alkoxy, alkenyloxy, alkylamino or dialkylamino groups, or are hydrogenated under the conditions of the hydrogenative amination, for example CC double or triple bonds. If polyfunctional aldehydes or keto aldehydes are to be aminated, control of the reaction conditions allows amino alcohols, cyclic amines or multiply aminated products to be obtained.

Preference is given, for example, to aminatively hydrogenating the following aldehydes:

formaldehyde, acetaldehyde, propionaldehyde, n-butyraldehyde, isobutyraldehyde, pivalaldehyde, n-pentanal, n-hexanal, 2-ethylhexanal, 2-methylpentanal, 3-methylpentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, 4-formyltetrahydropyran, 3-formyltetrahydrofuran, 5-formylvaleronitrile, citronellal, acrolein, methacrolein, ethylacrolein, citral, crotonaldehyde, 3-methoxypropionaldehyde, 3-aminopropionaldehyde, hydroxypivalaldehyde, dimethylolpropionaldehyde, dimethylolbutyraldehyde, furfural, glyoxal, glutaraldehyde and also hydroformylated oligomers and polymers. e.g. hydroformylated polyisobutene (polyisobutene aldehyde) or the oligomer obtained by metathesis of 1-pentene and cyclopentene and subsequent hydroformylation.

Aminating agents which can be used in the hydrogenative amination of alcohols, aldehydes or ketones in the presence of hydrogen include both ammonia and primary or secondary, aliphatic or cycloaliphatic or aromatic amines.

When ammonia is used as aminating agent, the alcoholic hydroxyl group or the aldehyde group or the ketone group is firstly converted into the primary amino group ($-NH_2$). The primary amine formed in this way can react with further alcohol or aldehyde or ketone to form the corresponding secondary amine and this can in turn react with further alcohol or aldehyde or ketone to form the corresponding, preferably symmetrical, tertiary amine. Depending on the composition of the reaction mixture or the feed stream (in the case of a continuous process) and the reaction conditions employed (pressure, temperature, reaction time (space velocity over the catalyst)), primary, secondary or tertiary amines can be prepared preferentially as desired in this way.

Polyhydric alcohols or dialdehydes or oligoaldehydes or diketones or oligoketones or keto aldehydes can in this way be converted by intramolecular hydrogenative amination into cyclic amines such as pyrrolidines, piperidines, hexamethylenimines, piperazines and morpholines.

Like ammonia, primary or secondary amines can be used as aminating agents.

These aminating agents are preferably used for preparing unsymmetrically substituted dialkylamines or trialkylamines, e.g. ethyldiisopropylamine and ethyldicyclohexylamine. For example, the following monoalkylamines and dialkylamines are used as aminating agents: methylamine, dimethylamine, ethylamine, diethylamine, n-propylamine, di-n-propylamine, isopropylamine, diisopropylamine, isopropylethylamine, n-butylamine, di-n-butylamine, s-butylamine, di-s-butylamine, isobutylamine, n-pentylamine, s-pentylamine, isopentylamine, n-hexylamine, s-hexylamine, isohexylamine, cyclohexylamine, aniline, toluidine, piperidine, morpholine and pyrrolidine.

Amines which are particularly preferably prepared by the process of the present invention are, for example, morpholine (from aminodiglycol), 6-dimethylamino-1-hexanol (from hexanediol and dimethylamine (DMA)), triethylamine (from ethanol and diethylamine (DEA)), dimethylethylamine (from ethanol and DMA), N-methylmorpholine (from diethylene glycol and monomethylamine (MMA)), N-methylpiperidine (from pentanediol and MMA), N-methylpiperazine (from diethanolamine and MMA), N,N'-dimethylpiperazine (from N-methyldiethanolamine and MMA), ethylenediamine (EDA) and diethylenetriamine (DETA) from monoethanolamine (MEOA), 2-ethylhexylamine and bis(2-ethylhexyl)amine (from 2-ethylhexanol and $NH_3$), tridecylamine and bis(tridecyl)amine (from tridecanol and $NH_3$), n-octylamine (from n-octanol and $NH_3$), 1,2-propylenediamine (from 2-hydroxypropylamine and $NH_3$), 1-diethylamino-4-aminopentane (from 1-diethylamino-4-hydroxypentane and $NH_3$), dimethylcyclohexylamine (from cyclohexanone and DMA), polyisobutenamine (from Pib-Oxo and $NH_3$), propylamines (e.g. monopropylamine/dipropylamine, dimethylpropylamine) (from propionaldehyde or n-propanol and $NH_3$ or DMA).

The aminating agent can be used in stoichiometric, substoichiometric or superstoichiometric amounts, based on the alcoholic hydroxyl group or aldehyde group or keto group to be aminated.

In the case of the amination of alcohols, aldehydes or ketones using primary or secondary amines, the amine is preferably used in an approximately stoichiometric amount or slightly superstoichiometric amount per mole of alcoholic hydroxyl group, aldehyde group or keto group to be aminated.

Ammonia specifically is generally used in a 1.5- to 250-fold, preferably 2- to 100-fold, in particular 2- to 10-fold, molar excess per mole of alcoholic hydroxyl group, aldehyde group or keto group to be reacted. Higher excesses both of ammonia and of primary or secondary amines are also possible.

The process of the present invention can be carried out batchwise or preferably continuously as follows, with the catalyst preferably being present in the reactor as a fixed bed. However, a fluidized-bed reaction with swirling up and down motion of catalyst material is likewise possible.

The amination of the primary or secondary alcohol groups, aldehyde groups or ketone groups of the starting material can be carried out in the liquid phase or in the gas phase. Preference is given to a fixed-bed process in the gas phase.

When the reaction is carried out in the liquid phase, the starting materials (alcohol, aldehyde or ketone plus ammonia or amine) are simultaneously passed in the liquid phase at pressures of generally from 5 to 30 MPa (50–300 bar), preferably from 5 to 25 MPa, particularly preferably from 15 to 25 MPa, and temperatures of generally from 80 to 300° C., preferably from 120 to 270° C., particularly preferably from 130 to 250° C., in particular from 170 to 230° C., including hydrogen, over the catalyst which is usually present in a fixed-bed reactor which is preferably heated externally. Both downflow mode operation and upflow mode operation are possible. The space velocity over the catalyst is generally in the range from 0.05 to 5 kg, preferably from 0.1 to 2 kg, particularly preferably from 0.2 to 0.6, kg, of alcohol, aldehyde or ketone per liter of catalyst (bed volume) and hour. If desired, the starting materials can be diluted with a suitable solvent such as tetrahydrofuran, dioxane, N-methylpyrrolidone or ethylene glycol dimethyl ether. It is advantageous to preheat the reactants before they are fed into the reactor vessel, preferably to the reaction temperature.

When the reaction is carried out in the gas phase, the gaseous starting materials (alcohol, aldehyde or ketone plus ammonia or amine) are passed in a gas stream, preferably hydrogen, which is sufficiently large for vaporization at pressures of generally from 0.1 to 40 MPa (1–400 bar), preferably from 0.1 to 10 MPa, particularly preferably from 0.1 to 5 MPa, in the presence of hydrogen over the catalyst. The temperatures for the amination of alcohols are generally from 80 to 300° C., preferably 120 to 270° C., particularly preferably from 160 to 250° C. The reaction temperatures in the hydrogenative amination of aldehydes and ketones are generally from 80 to 300° C., preferably from 100 to 250° C. The gaseous feed stream can be passed through the fixed catalyst bed from above or from below. The gas stream required is preferably obtained by means of a gas recycle mode of operation. The space velocity over the catalyst is generally in the range from 0.01 to 2 kg, preferably, from 0.05 to 0.5, kg, of alcohol, aldehyde or ketone per liter of catalyst (bed volume) and hour.

The hydrogen is generally introduced into the reaction in an amount of from 5 to 400 l, preferably from 50 to 200 l, per mole of alcohol, aldehyde or ketone component, with the number of liters indicated being in each case based on standard conditions (S.T.P.). The amination of aldehydes or ketones differs from the procedure in the amination of alcohols by at least stoichiometric amounts of hydrogen having to be present in the amination of aldehydes and ketones.

It is possible to employ higher temperatures and higher total pressures both when the reaction is carried out in the liquid phase and when the reaction is carried out in the gas phase. The pressure in the reaction vessel, which is the sum of the partial pressures of the aminating agent, the alcohol, aldehyde or ketone and the reaction products formed and any solvent employed at the temperatures indicated, is advantageously increased to the desired reaction pressure by injection of hydrogen.

The excess aminating agent can be circulated together with the hydrogen both when the reaction is carried out continuously in the liquid phase and when it is carried out continuously in the gas phase.

If the catalyst is present as a fixed bed, it can be advantageous in terms of the selectivity of the reaction for the shaped catalyst bodies in the reactor to be mixed with inert shaped bodies so as to "dilute" them. The proportion of inert shaped bodies in such catalyst beds can be from 20 to 80% by volume, preferably from 30 to 60% by volume and in particular from 40 to 50% by volume.

The water of reaction formed during the reaction (in each case one mol per mol of reacted alcohol group, aldehyde group or keto group) generally does not have an adverse effect on the degree of conversion, the reaction rate, the selectivity and the operating life of the catalyst and is therefore advantageously removed from the reaction product only on work-up of this, e.g. by distillation.

After the reaction product mixture has advantageously been depressurized, the excess aminating agent and the hydrogen are removed from it and the amination products obtained are purified by distillation or rectification, liquid extraction or crystallization. The excess aminating agent and the hydrogen are advantageously returned to the reaction zone. The same applies to any incompletely reacted alcohol, aldehyde or ketone component.

The amines prepared using the process of the present invention are suitable, inter alia, as intermediates in the production of fuel additives (U.S. Pat. No. 3,275,554; DE-A-21 25 039 and DE-A-36 11 230), surfactants, drugs and crop protection agents, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerators and/or emulsifiers.

BRIEF DESCRIPTION OF THE DRAWING(S)

FIG. 1 shows the compressive strength alterations with time of use of a catalyst A according to the present invention and a comparative catalyst B

EXAMPLES

Preparation of Catalysts

Catalyst A (According to the Present Invention):

Catalyst A was prepared as follows by precipitation of the components Cu, Co and Ni onto monoclinic zirconium dioxide which has been initially placed in the precipitation vessel:

A suspension of 155 g of monoclinic zirconium dioxide powder (BET=105 m$^2$ g$^{-1}$) in 2 l of water was placed in a stirrable glass vessel and heated to 70° C. while stirring. A solution of 190.1 g of Cu(NO$_3$)$_2$×2.5 H$_2$O, 561.9 g of Ni(NO$_3$)$_2$×6 H$_2$O and 543.7 g of Co(NO$_3$)$_2$×6 H$_2$O in 2.8 l of water was then added dropwise over a period of 30 minutes. The pH was kept constant at 6.0 by simultaneous dropwise addition of a 20% strength sodium carbonate solution (700 g of Na$_2$CO$_3$ in 2.8 l of water). After addition of the solutions, the mixture was stirred at 70° C. for another 1 hour and the pH was finally increased to 7.4 by addition of sodium carbonate solution. The suspension was pumped onto a suction filter and washed with 100 l of water. The filter cake was dried at 200° C. in a drying oven fro 16 hours, subsequently comminuted to a particle size of <1.6 mm and calcined at 400° C. in a stream of air (150 l/h) in a rotary tube furnace for 2 hours.

The catalyst powder obtained in this way had the composition:

28% by weight of Ni, calculated as NiO,
28% by weight of Co, calculated as CoO,
11% by weight of Cu, calculated as CuO, and
33% by weight of Zr, calculated as ZrO$_2$.

The powder was admixed with 3% by weight of graphite, compacted, once again comminuted to <1.6 mm and finally pressed to form 4.75×3 mm pellets. The pellets were then calcined at 400° C. in air in a muffle furnace for 2 hours. The pellets were then reduced in a stream of hydrogen and nitrogen in a reduction column, firstly at 150° C. for 6 hours and then at 280° C. for 6 hours. After cooling to room temperature, the pellets were passivated in a stream of diluted air.

Catalyst B (Comparative Catalyst):

The comparative catalyst was prepared in the same way as the catalyst A according to the present invention, except that no monoclinic zirconium dioxide was initially placed in the precipitation vessel. Instead, 775 g of a zirconium acetate solution having a concentration of 20% by weight, calculated as ZrO$_2$, (based on the weight of the zirconium acetate solution) was added to the metal salt solution comprising copper, cobalt and nickel nitrates (coprecipitation). The further preparation was analogous to that of catalyst A. The catalyst powder obtained analogously had the same composition as that described for catalyst A.

Example 1

To test the mechanical stability of the catalysts A and B under the reaction conditions of the hydrogenative amination of hydroformylated polyisobutene (PiB-Oxo; molar mass: 1000) to the primary amine PIBA according to the reaction equation

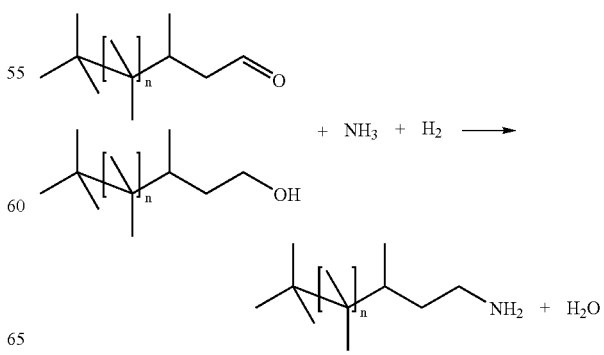

the catalysts were subjected to a boiling test in an autoclave (autoclave test) in which the reaction conditions were set as follows:

20 g of catalyst were placed in a wire basket in a stirring autoclave. 150 ml of a PIBA/Mihagol (50/50) solution were added thereto, so that the catalyst pellets were well covered with liquid. The autoclave was closed, flushed with nitrogen, the stirrer was set to a speed of 700 rpm, 50 bar of $H_2$ were injected and the contents of the autoclave were heated to 200° C. The pressure was then set to 200 bar by additional injection of $H_2$. Under these conditions, the catalyst was treated for different periods of time. The autoclave was subsequently cooled, carefully depressurized and the mechanical stability of the catalyst was determined by measuring the lateral compressive strength (LCS).

For this purpose, the catalyst pellet was subjected to an increasing force on the cylindrical surface between two parallel plates until fracture occurred. The force recorded on fracture is the lateral compressive strength. The determination was carried out on a test apparatus from Zwick, Ulm, having a fixed rotating plate and a freely movable, vertical punch which pressed the shaped body against the fixed rotating plate. The freely movable punch was connected to a load cell to measure the force. The instrument was controlled by a computer which recorded and evaluated the measured values. 25 intact pellets (i.e. pellets which were crack-free and had no broken edges) were taken from a well mixed catalyst sample, their lateral compressive strength was determined and subsequently averaged.

In the accompanying FIG. 1, the lateral compressive strengths (unit: Newton, N) of the two catalysts A and B are plotted over the time of the autoclave test (in hours):

In the case of the catalyst B prepared by coprecipitation, the X-ray diffraction pattern after the boiling test indicated that the initially X-ray-amorphous $ZrO_2$ phase had been converted into tetragonal and monoclinic $ZrO_2$. In the case of catalyst A, no recrystallization (=change of modification) was found.

We claim:

1. A process for preparing an amine by reacting a primary or secondary alcohol, aldehyde or ketone with hydrogen and a nitrogen compound selected from the group consisting of ammonia and primary and secondary amines in the presence of a catalyst whose preparation has involved precipitation of catalytically active components onto monoclinic, tetragonal or cubic zirconium dioxide, wherein the catalytically active composition of the catalyst before treatment with hydrogen comprises from 20 to 65% by weight of oxygen-containing compounds of zirconium, calculated as $ZrO_2$, from 1 to 30% by weight of oxygen-containing compounds of copper, calculated as CuO, from 15 to 50% by weight of oxygen-containing compounds of nickel, calculated as NiO, and from 15 to 50% by weight of oxygen-containing compounds of cobalt, calculated as CoO.

2. A process as claimed in claim 1, wherein the catalytically active components precipitated are salts of a metal selected from transition groups VIII and IB of the Periodic Table.

3. A process as claimed in claim 2, wherein the metal salts are basic salts which are sparingly soluble or insoluble in water.

4. A process as claimed in claim 2, wherein the salts are oxides, hydrated oxides, hydroxides, carbonates and/or hydrogencarbonates.

5. A process as claimed in claim 2, wherein the metal is selected from the group consisting of Fe, Go, Ni, Ru, Rh, Pd, Pt and Cu.

6. A process as claimed in claim 2, wherein the metal is selected from the group consisting of Cu, Ni and Co.

7. A process as claimed in claim 5, wherein the molar ratio of nickel to copper is greater than 1.

8. A process as claimed in claim 1, wherein the monoclinic, tetragonal or cubic zirconium dioxide contains one or more oxides of metals of transition groups IIIB or main group IIA of the Periodic Table.

9. A process as claimed in claim 1, wherein the reaction is carried out at from 80 to 300° C.

10. A process as claimed in claim 1, wherein the reaction is carried out in the liquid phase at pressures of from 5 to 30 MPa or in the gas phase at pressures of from 0.1 to 40 MPa.

11. A process as claimed in claim 1 for preparing an amine of the formula I

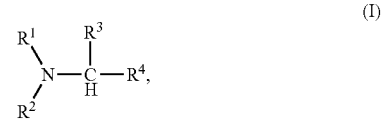

where $R^1$, $R^2$ are each hydrogen (H), alkyl, cycloalkyl, alkoxyalkyl, dialkylaminoalkyl, aryl, aralkyl or alkylaryl, or together form $-(CH_2)_j-X-(CH_2)_k-$, $R^3$, $R^4$ are each hydrogen (H), alkyl, cycloalkyl, hydroxyalkyl, aminoalkyl, hydroxyalkylaminoalkyl, alkoxyalkyl, dialkylaminoalkyl, alkylaminoalkyl, $R^5-$ $(OCR^6R^7CR^8R^9)_n-(OCR^6R^7)$, aryl, heteroaryl, aralkyl, heteroarylalkyl, alkylaryl, alkylheteroaryl or $Y-(CH_2)_m-NR^5-(CH_2)_q$, or together form $-(CH_2)_l-X-(CH_2)_m-$, or $R^2$ and $R^4$ together form $-(CH_2)_l-X-(CH_2)_m-$, $R^5$, $R^{10}$ are each hydrogen (H), alkyl or alkylphenyl, $R^6$, $R^7$, $R^8$, $R^9$ are each hydrogen (H), methyl or ethyl, X is $CH_2$, $CHR^5$, oxygen (O), sulfur (S) or $NR^5$, Y is $N(R^{10})_2$, hydroxy, $C_{2-20}$-alkylaminoalkyl or $C_{3-20}$-dialkylaminoalkyl, n is an integer from 1 to 30 and j, k, l, m, q are each an integer from 1 to 4, by reacting a primary or secondary alcohol of the formula II

or aldehyde or ketone of the formula VI or VII

with a nitrogen compound of the formula III

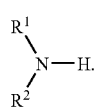
(III)

12. The process as claimed in claim 11, wherein
$R^1$, $R^2$ are each hydrogen (H), $C_{1-20}$-alkyl, $C_{3-12}$-cycloalkyl, $C_{2-30}$-alkoxyalkyl, $C_{3-30}$-dialkylaminoalkyl, aryl, $C_{7-20}$-aralkyl or $C_{7-20}$-alkylaryl, or together form —$(CH_2)_j$—X—$(CH_2)_k$—, $R^3$, $R^4$ are each hydrogen (H), $C_{1-200}$-alkyl, $C_{3-12}$-cycloalkyl, $C_{1-20}$-hydroxyalkyl, $C_{1-20}$-aminoalkyl, $C_{2-20}$-hydroxyalkylaminoalkyl, $C_{2-30}$-alkoxyalkyl, $C_{3-30}$-dialkylaminoalkyl, $C_{2-30}$-alkylaminoalkyl, $R^5$—$(OCR^6R^7CR^8R^9)_n$—$(OCR^6R^7)$, aryl, heteroaryl, $C_{7-20}$-aralkyl, $C_{4-20}$heteroarylalkyl, $C_{7-20}$-alkylaryl, $C_{4-20}$-alkylheteroaryl or Y—$(CH_2)_m$—$NR^5$—$(CH_2)_q$, or together form —$(CH_2)_l$—X—$(CH_2)_m$—, or $R^2$ and $R^4$ together form —$(CH_2)_l$—X—$(CH_2)_m$—, and $R^5$, $R^{10}$ are each hydrogen (H), $C_{1-4}$-alkyl or $C_{7-40}$-alkylphenyl.

* * * * *

UNITED STATES PATENT AND TRADEMARK OFFICE
CERTIFICATE OF CORRECTION

PATENT NO.         : 7,034,186 B2                                     Page 1 of 1
APPLICATION NO. : 10/731158
DATED              : April 25, 2006
INVENTOR(S)        : Gerlach et al.

It is certified that error appears in the above-identified patent and that said Letters Patent is hereby corrected as shown below:

In claim 5, column 16 at indicated line 2: "Fe, Go, Ni," should read --Fe, Co, Ni,--

Signed and Sealed this

Seventeenth Day of April, 2007

JON W. DUDAS
*Director of the United States Patent and Trademark Office*